United States Patent [19]

Curtis et al.

[11] Patent Number: 5,331,089
[45] Date of Patent: Jul. 19, 1994

[54] PEPTIDES USEFUL AS TACHYKININ AGONISTS

[75] Inventors: Neil R. Curtis, Royston; Brian J. Williams, Great Dunmow, both of England

[73] Assignee: Merck Sharpe & Dohme, Ltd., Hoddesdon

[21] Appl. No.: 993,493

[22] Filed: Dec. 17, 1992

Related U.S. Application Data

[63] Continuation of Ser. No. 854,193, Mar. 20, 1992, abandoned, which is a continuation of Ser. No. 716,425, Jun. 17, 1991, abandoned, which is a continuation of Ser. No. 324,170, Mar. 16, 1989, abandoned.

[30] Foreign Application Priority Data

Mar. 25, 1988 [GB] United Kingdom ................. 8807246

[51] Int. Cl.$^5$ ........................... C07K 7/54; C07K 7/06; C07K 7/08
[52] U.S. Cl. ................................... 530/317; 530/323; 530/327; 530/329
[58] Field of Search ............... 530/317, 323, 327, 329; 514/9, 10, 11, 14, 16, 17, 803, 825, 826, 886

[56] References Cited

U.S. PATENT DOCUMENTS

| | | | |
|---|---|---|---|
| 4,501,733 | 2/1985 | Hörig et al. | 514/17 |
| 4,665,157 | 5/1987 | Wright | 530/328 |
| 4,680,283 | 7/1987 | Veber et al. | 530/330 |

OTHER PUBLICATIONS

Aldrich-Catalog Handbook of Fine Chemicals, p. 1177 1986 Aldrich Chemical Co.
Rudinger, Peptide Hormones, Parsons (Ed.) U. Park Press, Baltimore, pp. 1-7 (1976).
Cascieri et al., Molecular Pharmacology, vol. 29, pp. 34-38 (1986).
Kirk-Othmer, Encyclopedia of Chemical Technology (New York, John Wiley and Sons), 3rd Ed., vol. 2, p. 809 (1978).

*Primary Examiner*—Christina Y. Chan
*Attorney, Agent, or Firm*—Robert J. North; Melvin Winokur

[57] ABSTRACT

A class of monomeric or dimeric peptides containing a specific hexa- or heptapeptide unit in either linear or cyclic form are active tachykinin antagonists and are therefore useful in disease states in which these peptides have been implicated, such as allergic conditions, inflammation, migraine, arthritis and CNS disorders.

9 Claims, No Drawings

PEPTIDES USEFUL AS TACHYKININ AGONISTS

CROSS-REFERENCE TO RELATED APPLICATIONS

The instant case is a continuation application of U.S. application Ser. No. 07/854,193, filed Mar. 20, 1992, now abandoned, which in turn is a continuation of U.S. application Ser. No. 07/716,425, filed Jun. 17, 1991, now abandoned, which in turn is a continuation of U.S. application Ser. No. 07/324,170, filed Mar. 16, 1989, now abandoned.

This invention relates to a class of peptide compounds, and in particular to compounds containing a specific hexa- or heptapeptide unit in either linear or cyclic form, which are useful as tachykinin antagonists.

The tachykinins are a group of naturally occurring peptides found widely distributed throughout mammalian tissues, both within the central nervous system and in peripheral nervous and circulatory systems. For example, a mammalian tachykinin, Substance P, is believed inter alia to be involved in neurotransmission of pain sensations. The tachykinin antagonists of this invention are useful in disease states in which these peptides have been implicated, such as allergic conditions, inflammation, migraine, arthritis and CNS disorders.

The structures of three known mammalian tachykinins are as follows:
Substance P:
Arg-Pro-Lys-Pro-Gln-Gln-Phe-Phe-Gly-Leu-Met-NH$_2$
Neurokinin A:
His-Lys-Thr-Asp-Ser-Phe-Val-Gly-Leu-Met-NH$_2$
Neurokinin B:
Asp-Met-His-Asp-Phe-Phe-Val-Gly-Leu-Met-NH$_2$ Certain inhibitors of tachykinins have been described in U.S. Pat. No. 4,501,733, by replacing residues in the Substance P sequence by Trp residues.

The compounds of the present invention have a high degree of receptor selectivity in their inhibition of tachykinins; and have an improved stability towards enzymatic degradation.

The present invention provides a peptide of formula (I):

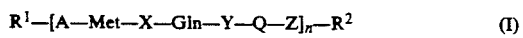

in which any of the amide linkages between the amino acids may be N-methylated; and wherein
A represents Leu;
X represents Gly, or a bond;
Y represents an aromatic amino acid residue;
Q represents a hydrophobic amino acid residue;
Z represents Gly;
n is 1 or 2;
$R^1$ represents an amino blocking group; and
$R^2$ represents a carboxyl blocking group; or
$R^1$ and $R^2$ together represent a bond between the groups Z and A; or
Z and A, optionally together with the bond $R^1$—$R^2$ form a moiety of formula (II):

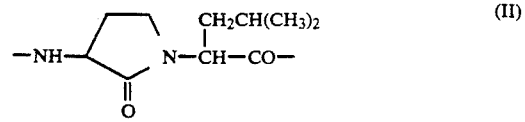

The aromatic amino acid residue Y may be, for example, Trp, D-Trp, Phe, Tyr or naphthylalanine (Npa). Preferably Y represents Trp, D-Trp, Phe or Npa.

The group Q is a hydrophobic amino acid residue. In particular, the group Q has an aromatic or branched alkyl side-chain. Suitable values for the group Q include Trp, D-Trp, Phe, Tyr, Npa, Ile and Val. Preferably, Q is Phe.

Any of the amide bonds between the amino acid sequence in formula (I) may additionally have a methyl group on the nitrogen atom. In particular the amide bond between the groups Y and Q may be N-methylated. As the nitrogen atom in that linkage is derived from the Q group, the compound is prepared by employing an N-methyl amino acid, e.g. N-methyl-Phe, at that position.

The novelty of the compounds of this invention resides in the sequence of amino acids set out in formula (I), which may be in linear or cyclic form, and in either case may possess either one or two sequences (i.e. n=1 or 2 respectively). It is believed that the critical sequence of amino acids is such that the conformation of the resulting peptide enables the molecule to fit into a tachykinin-type receptor. Variation of the amino acid residues in the compounds of this invention allows for specificity for different tachykinin receptors. The cyclic peptides of this invention are preferred, as the conformation thereof is restricted.

Nevertheless the conformation of the peptide is not the only requirement for activity; the presence of particular groups, especially the glutamine residue, is essential.

In the linear peptides of formula (I), both ends of the molecule must be blocked, or derivatised. At the amino end of the linear peptide, the group A will represent leucine. Any conventional blocking group may be employed. Suitable amino-blocking groups $R^1$ for this position include groups of formula —COR$^3$, —CO$_2$R$^3$ and —CONH$_2$, wherein $R^3$ represents a hydrocarbon group, especially a C$_{1-6}$ alkyl group such as methyl, ethyl, propyl or butyl; an aryl group such as phenyl; or an aralkyl group such as benzyl. Together with the amino group of the leucine residue, these blocking groups will result in the N-terminal group of the peptide being an amide group —NHCOR$^3$, a urethane group —NHCO$_2$R$^3$, or a urea group —NHCONH$_2$. It is also possible to achieve a non-basic terminal group by removing the amino group of the leucine residue, i.e. by employing desaminoleucine as the group A—$R^1$. Preferred groups $R^1$ are acetyl and benzyloxycarbonyl.

Suitable C-terminal blocking groups $R^2$ for the linear peptide of formula (I), when Z=Gly, include groups which can derivatise the carboxyl group, such as —NR$^4$R$^5$ or —NR$^6$NHR$^7$, wherein R$^4$ and R$^5$ independently represent hydrogen or hydrocarbon; and R$^6$ and R$^7$ independently represent hydrogen, hydrocarbon, acyl or alkoxycarbonyl. Suitable hydrocarbon groups are those specified for the group R$^3$ above. A preferred group $R^2$ is amino, so that the C-terminal group on the glycine residue is —CONH$_2$.

In the dimeric forms of both the linear and cyclic peptides, i.e. when n=2, the linkage between the monomeric units may be either Gly-Leu or the lactam group of formula (II) above, which is derived from glycine and leucine. The abbreviation used for the moiety of formula (II) is Gly[ANC-2]Leu.

One sub-class of compounds of this invention, when Q is Phe, is represented by formula (III):

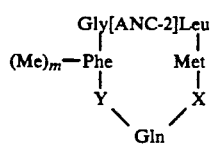   (III)

wherein m is zero or 1; Y is as defined with respect to formula (I), especially Trp, D-Trp, Phe or Npa; and X represents a bond or Gly.

Specific compounds of this invention are: cyclo(Gln-Trp-Phe-(R)Gly[ANC-2]Leu-Met); cyclo(Gln-Npa-Phe-(R)Gly[ANC-2]Leu-Met); cyclo(Gln-Trp-Phe-Gly-Leu-Met); cyclo(Gly-Gln-Trp-Phe-(R)Gly[ANC-2]Leu-Met); cyclo(Gln-D-Trp-(N-Me)Phe-(R)Gly[ANC-2]Leu-Met); cyclo(Gln-D-Trp-(N-Me)-Phe-(R)Gly[ANC-2]Leu-Met)$_2$; acetyl-Leu-Met-Gln-Trp-Phe-Gly-NH$_2$; cyclo(Gly-Gln-Phe-Phe-(R)Gly[ANC-2]Leu-Met); cyclo(Gly-Gln-D-Trp-Phe-(R)Gly[ANC-2]Leu-Met); cyclo(Gly-Gln-Tyr-Phe-(R)Gly[ANC-2]Leu-Met); and cyclo(Gln-Phe-Phe-(R)Gly[ANC-2]Leu-Met).

The abbreviated designations for amino acid residues used throughout this specification are as follows: By the term (R)Gly[ANC-2]Leu is meant a two carbon bridge between the alpha-carbon of the first residue, i.e. glycine, of a dipeptide to the alpha-nitrogen (N') of the second residue, i.e. leucine, of the same peptide. Chirality is imparted to the glycine residue which here is indicated by (R). This nomenclature is taken from the prior art citation, Molecular Pharmacology, Vol. 29, pp. 34–38 (1986).

| Lys   | L-lysine          |
|-------|-------------------|
| Phe   | L-phenylalanine   |
| Trp   | L-tryptophan      |
| D-Trp | D-tryptophan      |
| Npa   | L-naphthylalanine |
| Tyr   | L-tyrosine        |
| Val   | L-valine          |
| Ile   | L-isoleucine      |
| Gln   | L-glutamine       |
| Met   | L-methionine      |

The peptides of the present invention may be prepared from their constituent amino acids by standard methods of protein synthesis, e.g. Schroeder et al., "The Peptides", Vol I Academic Press, 1965; or Bodanszky et al., "Peptide Synthesis", Interscience Publishers, 1966; or McOmie (ed.), "Protective Groups in Organic Chemistry", Plenum Press, 1973; or George Barany and R. B. Merrifield, "The Peptides: Analysis, Synthesis, Biology", 2 Chapter 1, Academic Press, 1980.

A preferred method for the preparation of the peptides of this invention is the solid phase method, described by Atherton et al. in *Bioorg. Chem.*, 1979, 8, 351; or Merrifield in *J. Am. Chem. Soc.*, 1963, 85, 2149–2154. In this method the C-terminal amino acid, and then sequentially the other amino acid residues, are coupled to a carrier resin and, when the sequence is complete, the carrier resin is split off.

In the process of the present invention a preferred polyamide resin is a polydimethylacrylamide resin functionalised with monomers containing safcosine methyl ester functional moieties. Advantageously, the resin is first coupled to an N-blocked alanine derivative, such as Fmoc-Ala, to which a functional handle and the remaining amino acids can be coupled and then removed when the sequence is complete.

For the preparation of a linear peptide of this invention the C-terminal group, viz. glycine, is first coupled to the (4-hydroxymethylbenzoyl)alanylresin. After the remaining amino acids have been introduced, the peptide chain may be cleaved from the resin by treatment with methanol saturated with ammonia to give a product of formula (I) in which n is 1 and R$^2$ represents —NH$_2$. Alternatively the peptide chain may be cleaved from the resin by treatment with hydrazine to give a valuable intermediate of formula (IV):

R$^1$—Leu—Met—X—Gln—Y—Q—Gly—NHNH$_2$   (IV),

The intermediate (IV) may be employed to couple to a second monomeric peptide chain to produce a dimeric product of formula (I) where n=2. Compound (IV) may also be cyclised to give a cyclic form of a peptide of formula (I) above.

For the preparation of the cyclic peptides of formula (I) in general, the first amino acid to be linked to the resin may be any of the residues in the polypeptide as the final product will be cyclised. It is convenient to use methionine as the initial group so that the final sequence which is cleaved from the resin, if hydrazine is employed, is an intermediate of formula (V) :

X—Gln—Y—Q—Z—A—Met—NHNH$_2$   (V)

Treatment of the hydrazide with iso-amyl nitrite produces an azide intermediate of formula X—Gln—Y—Q—Z—A—Met—N$_3$   (V)

which may be cyclo-condensed to provide a cyclic peptide of formula (I) above.

The Gly[ANC-2]Leu lactam moiety of formula (II) above may be prepared from Met-Leu by cycloalkylation of the methylsulphonium iodide derivative thereof as shown in formulae (VII)→(VIII):

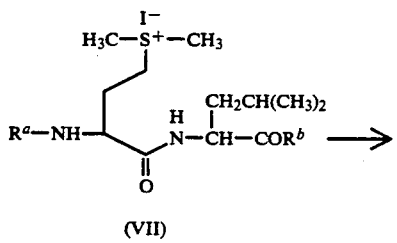

(VII)

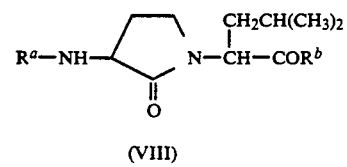

(VIII)

wherein $R^a$ and $R^b$ are removable protecting groups. The reaction may be conducted in an inert organic solvent such as dimethylformamide/methylene dichloride, with a strong base such as sodium hydride or n-butyl lithium.

In a further aspect of this invention, there is provided a pharmaceutical composition comprising a peptide of formula (I) above together with a pharmaceutically acceptable carrier.

The peptides of this invention or their amides, lower alkyl esters, metal salts or acid addition salts with pharmaceutically acceptable acids, are administered to a mammalian species, systemically, either by intravenous, subcutaneous or intramuscular injection, or by sublingual or nasal administration, in compositions in conjunction with pharmaceutically acceptable vehicles or carriers. For administration by injection or by the nasal route it is preferred to use the peptides in solution in a sterile aqueous vehicle which may also contain other solutes such as buffers or preservatives as well as sufficient quantities of pharmaceutically acceptable salts or of glucose to make the solution isotonic. In addition, when the above compositions are intended for use as sprays for nasal administration they may also contain small amounts of a pharmaceutically acceptable surface-active agent to ensure rapid absorption of the respective peptide by the nasal mucosa. Examples of such surface-active agents are polysorbate 80 (TWEEN 80), benzalkonium chloride, bile salts such as sodium glycocholate, dioctyl sodium sulphosuccinate (AEROSOL OT), and the like. For sublingual administration it is preferred to formulate the peptides of this invention as rapidly dissolving tablets together with solid excipients or carriers such as lactose. Examples of such excipients or carriers are found in standard pharmaceutical texts, e.g. in Remington's Pharmaceutical Sciences, Mack Publishing Company, 1970. Intranasal or sublingual administration may be less precise than intravenous injection but it may be a more convenient form of treatment.

Suitable pharmaceutical compositions containing the active ingredient can be in the form of creams, ointments, jellies, solutions, suspensions, nasal or inhalant sprays or drops, eye drops, or pressurized or non-pressurized dispersible powders.

For example, aqueous suspensions can be used containing the active ingredient in admixture with excipients suitable for the manufacture of aqueous suspensions. Such excipients include suspending agents, for example sodium carboxymethylcellulose, methylcellulose, hydroxypropylmethylcellulose, sodium alginate, polyvinylpyrrolidone, gum tragacanth or gum acacia; and dispersing or wetting agents such as naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives, for example ethyl or n-propyl p-hydroxybenzoate, one or more colouring agents, one or more flayouting agents, and one or more sweetening agents, such as sucrose or saccharin.

Oily suspensions can also be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid.

Pressurized or non-pressurized dispersible powders and granules suitable for preparation of an aqueous suspension by the addition of water provide the active ingredient in admixture with a dispersing or wetting agent and a suspending agent; one or more preservatives can be employed. Suitable dispersing or wetting agents and suspending agents are exemplified by those already mentioned above. Additional excipients, for example sweetening, flayouting and colouring agents, may also be included.

The amount of the peptide of formula (I) for use in the present compositions will vary depending, for example, on the condition being treated, the size and kind of mammal and the route of administration. In general doses of 0.1 to 50 mg/kg/day are satisfactory.

Biological Data

The activity of the compounds of the accompanying Examples as tachykinin receptor antagonists was evaluated using the following method:

The Isolated Rat Vas Deferens Preparation

The tachykinin receptor present in the longitudinal muscle of the rat vas deferens has been characterised, using natural and synthetic tachykinins, as 'NK-2'. This preparation is therefore used to determine the selectivity and potency of the peptides for this receptor subtype.

Method

Male Wistar rats weighing 200–300 g are killed by decapitation. The vas deferens is dissected free from the surrounding connective tissue and suspended in a 3 ml organ bath under an initial resting tension of 1 g. The tissue is maintained at 37° C. in modified KREBS HENSALEIT solution (NaCl 118.4, KCl 4.7, $CaCl_2$ 2.5, $KH_2PO_4$ 1.18, $MgSO_4.7H_2O$ 1.19, $NaHCO_3$ 25.0, D-glucose 11.1 mM), which is continuously gassed with a mixture of 95% $O_2$ and 5% $CO_2$. Field stimulated responses are elicited by trains of pulses delivered for 1 second every 20 seconds (7 Hz, 70-80 V, individual pulse duration 0.5 ms). The longitudinal contraction of the vas deferens is recorded isometrically using a UFI DYNAMOMETER strain transducer and displayed on a flat bed chart recorder. Contractions remain reasonably constant for 3–4 hours with no spontaneous changes in resting tension. A dose-cycle of 10–15 minutes is used, drug contact time being about 3–5 minutes.

In all experiments eledoisin is used as a standard agonist. Eledoisin, in the dose range $10^{-8}$–$3\times10^{-6}$M, produces a dose-related increase in twitch height and, to a lesser extent, basal tension. A second dose-response curve is then constructed to the peptide under investigation.

To determine the potency of each peptide as an NK-2 antagonist, the test compound is added to the bathing medium, at an appropriate concentration, 20-30 minutes before the first dose of the second eledoisin dose-response curve. Thereafter addition of the test compound 5-10 minutes before the eledoisin dose is sufficient. The percentage increase in twitch produced by eledoisin in the presence and absence of the antagonist is expressed as a percentage of the maximum response of each individual dose-response curve. Thus all dose-response curves have the same maximum. From the dose ratio an estimate of the $pA_2$ (-$logK_b$) for each test compound can be determined:

$pA_2 = log[(DR-1)/(antagonist\ conc.)]$

The results are summarised in Table I below:

TABLE 1

| Compound of Example No. | $pA_2$ (against eledoisin) |
| --- | --- |
| 1 | 6.7 |
| 2 | 5.6 |
| 3 | 8.0 |
| 4 | 6.0 |
| 5a | 6.4 |
| 5b | 5.1 |
| 6 | 6.8 |
| 7 | 4.6 |
| 8 | 5.0 |
| 9 | 5.0 |
| 10 | 4.8 |

The following Examples illustrate the preparation of compounds of this invention.

EXAMPLE 1

Cyclo(Gln-Trp-Phe-(R)Gly[ANC-2]Leu-Met)

a) Preparation of Boc-Gln-Trp-Phe-(R)Gly [ANC-2]Leu-Met-NHNH$_2$ (I)

The preparation of Example 1 serves as a general illustration for the method of preparation of the intermediate hydrazides for Examples 1, 2, 3a, 4, 5, 7,8,9,10.

Polydimethylacrylamide resin (Cambridge Research Biochemicals, 2.96g, 2.96 mmol of functional safcosine methyl ester) was treated with diamino ethane for 16 h. The resin was washed on a Vega TM 250$^c$ solid phase peptide synthesizer with wash cycle A (DMF, 10×1 min; 10% Diisopropylethylamine in DMF, 3×1 min; DMF, 10×1 min). To the resin was added the preformed symmetrical anhydride of Fmoc-L-Ala (8.9 mmol) dissolved in DMF (20 ml) for 40 min. The resin was washed with wash cycle B (DMF, 10×1 min; 20% piperidine in DMF, 3 min +7 min; DMF 10×1 min) followed by addition of the preformed symmetrical anhydride of 4-hydroxymethylbenzoic acid (8.9 mmol) dissolved in DMF (20 ml) for 40 min. After the resin had been washed with wash cycle A the hydroxymethyl groups attached to the resin were acylated with the preformed symmetrical anhydride of Fmoc-Met (8.9 mmol) in the presence of N-methylmorpholine (8.9 mmol) and catalytic 4-dimethylaminopyridine (0.89 mmol) in DMF (20 ml) for 20 min. The resin was deprotected with wash cycle B and acylated with the lactam unit (R)-(3-butoxycarbonylamino-2-oxo-1-pyrrolidinyl)-5)-2(4-methyl)pentanoic acid (Boc-(R)Gly[ANC-2]LeuOH (II)(5.9 mmol). (previously preactivated with DCC 5.9 mmol and hydroxybenzotriazole (HOBt. 5.9 mmol) for 30 min at 0° C. in CH$_2$Cl$_2$; DMF (2:1)) in DMF (25 min) for 16 h. Excess reagents were then removed using wash cycle A followed by washing with CH$_2$Cl$_2$. The t-butoxycarbonyl group was removed by treatment of the resin with TFA: CH$_2$Cl$_2$ (1:1) containing 1% ethanedithiol (5 min and 25 min). The resin was then washed with CH$_2$Cl$_2$ followed by wash cycle A and coupled with the preformed symmetrical arthydride of Fmoc-Phe (8.9 mmol) for 1.25 h. After washing with DMF (5×1 min) the resin was divided into two separate portions. One portion (2.4 mmol) was used for the preparation of the title compound. This was deprotected using wash cycle B followed by acylation with the symmetrical anhydride of Fmoc-Trp (7.08 mmol) for 45 min in DMF (15 ml). The resin was washed with wash cycle B. acylated with BocGln-ONp (7.10 mmol) in the presence of HOBt (7.14 mmol) in DMF (30 ml) for 120 min. followed by washing with wash cycle A. Finally the resin was washed successively with CH$_2$Cl$_2$ and diethylether before being dried under the vacuum of an oil pump. This gave a resin (4.38 g, 1.49 mmol (Ala) which by amino acid analysis gave Glu (0.91), Ala (1.00), Met (0.80), Phe (0.92) (see footnote).

The crude peptide hydrazide was obtained by treatment of the resin with 5% hydrazinc hydrate in methanol (70 ml) for 16 h. The solution was filtered and evaporated to dryness followed by desiccation of the residue under the vaccum of an oil pump over concentrated sulfuric acid. The protected peptide hydrazide (I) was obtained 1.71 g, hplc ($R_t$=16.2 min, estimated purity ca 95%).

b) Preparation of cyclo (Gln-Trp-Phe(R)Gly [ANC-2]Leu-Met)

The protected peptide hydrazide (I, 1.69go 1.83 mmol) was treated with anhydrous TFA (100 ml) for 30 min. Evaporation gave a foam which was dissolved in DMF (40 ml) and cooled to −25° C. under an atmosphere of nitrogen. 12.7M HCl in THF (0.72 ml) was added followed by isopentylnitrite (0.37 ml, 2.75 mmol) and the. resultant solution stirred at −25° C. for 2 h (hplc, $R_t$=13.0 min). Precooled (−25° C.) DMF (3000 ml) was added to the solution and triethylamine added until pH =8.5 (ca 10 ml). The solution was left stirring at −25° C. for 20 h then the DMF was removed by evaporation. The residue, dissolved in CHCl$_3$ (175 ml), was washed with water (2×175 ml) and each aqueous wash was back extracted with fresh CHCl$_3$ (50 ml). The combined CHCl$_3$ phases were dried over Na$_2$SO$_4$ and evaporated to dryness. The residue was chromatographed on silica gel (E. MERCK, LOBAR, LITCOPREP, Size C) eluting the product with a linear gradient from CHCl$_3$ (500 ml) to CHCl$_3$:MeOH:AcOH (85:10:5,500 ml) at 5.4 ml/min, collecting fractions of 2 min. The fractions containing product (46–51) were combined, evaporated and chromatographed in three separate portions on reverse phase chromatography (E. MERCK, LOBAR, LICHOPREP, RP-8, Size C). The product was eluted with a linear gradient from H$_2$O:CH$_3$CN:TFA (90:10:0.1. 1000 ml) to H$_2$O:CH$_3$CN:TFA (10:90:0.1, 1000 ml) at 5.4 ml/min collecting fractions of 2 min. The fractions which contained pure material (81–86 incl) were combined and freeze-dried to give 678 mg of the title compound. Amino acid analysis Glu (0.99) Met (0.99) Phe (1.02) (see footnote). Estimated purity by analytical hplc=92% FAB mass spec positive ion m/e=790 (m+H), negative ion m/e=788 (m - H).

EXAMPLE 2

Cyclo(Gln-Npa-Phe-(R)Gly[ANC-2]Leu-Met)

The N-butoxycarbonyl protected peptide hydrazide was prepared similarly to that described in example 1. Fmoc-Met, Boc(R)Gly[ANC-2]Leu OH and Fmoc-Phe were coupled onto the solid phase resin under conditions identical with those described in Example 1a. At the appropriate stage in the solid phase synthesis was coupled N-α-fluroenylmethylmethoxyearbonyl-L-(1-naphthyl)alanine (Fmoc-Npa, prepared from commercially available L-3-(1-naphthyl)alanine (chemalog) by treatment with fluorenylmethylchloroformate in aq. sodium carbonate, mp=181°–183° C., $[\alpha]_D^{22.5} = -78.6°$ C. (C=0.87 DMF)) as the preformed symmetrical anhydride for 1.25 h. Boc-Gln-ONP was finally coupled to the resin after prior removal of the Fmoc group (wash cycle B). The crude peptide hydrazide was obtained by treatment of the resin with 5% hydrazine hydrate in methanol for 16 h followed by filtration and evaporation of the filtrate and exhaustive drying in vacuo. Removal of the N-butoxycarbonyl group from the peptide hydrazide was performed with 2.3M- HCl dioxan followed by cyclization under analogous conditions to Example 1b. Purification of the crude cyclic peptide was performed using silica gel chromatography (E. MERCK, LOBAR size "C" column gradient from chloroform (1000 ml) to chloroform: methanol:acetic acid (85:10:5; 1000 ml) followed by recrystallization from ethylacetate hexane. The title compound had an estimated purity=98% (hplc) NMR ('H) DMSO $d_6$; consistent with structure: amino acid analysis gave Glu (1.03), Met (0.93), Phe (1.03), FAB mass spectroscopy (negative ion) m/e=728 (m).

EXAMPLE 3

Cyclo (Gln-Trp-Phe-Gly-Leu-Met)

Method 1

The resin bound peptide was prepared by the sequential coupling of Fmoc-Meto Fmoc-Leu, Fmoc-Gly, Fmoc-Phe, and Fmoc-Trp by preformed symmetrical anhydride and Boc-GlnONp active ester in an analogous fashion to that described in Example 1. The peptide was removed from the resin (5% hydrazine hydrate in methanol. 16 h) deprotected (2.3M HCl in dioxan, 45 min) and cyclized (as described in Example 1b). The crude cyclic peptide was purified using silica gel chromatography under gradient conditions (as described) and reverse-phase chromatography (ZORBAX ODS; 9.4 mm×25 cm; eluting with a linear gradient between 40–60% aqueous acetonitrile containing 0.05% trifluroacetic at 4 ml/min over 10 min). This gave the title compound of purity>98% (hplc), amino acid analysis gave Glu(0.96), Gly(1.03), Met(0.80), Leu(0.99), Phe(1.02).

Method 2

(a) Preparation of Resin-Bound Protected Peptide Fmoc-Leu-Met-Gln-Trp-Phe-Gly

The preparation of this intermediate serves as a general illustration for the method of preparation of both cyclic peptides containing the glycyl amino acid residue and also linear peptides (Example 6).

Polydimethylacrylamide resin (1.1 meg/g, 5 mmol) was functionalised as in Example 1 and sequentially acylated with the preformed symmetrical anhydrides of Fmoc-Ala (15 mmol, 30.min), 4-hydroxymethylbenzoic acid (15 mmol, 60 min)o Fmoc-Gly (30 mmol, 60 min) in the presence of DMAP (3 mmol) and NMM (30 mmol), Fmoc-Phe (15 min 30 min), and Fmoc-Trp (10.6 mmol, 40 min). Acylation of the glutamine residue was performed by Fmoc-Gln-ONP (15 mmol) and hydroxybenzotriazole (15 mmol) for 30 min and finally acylation of the resin by the preformed symmetrical anhydrides of Fmoc-Met (15 mmol, 30 min) and Fmoc-Leu (15 mmol, 45 min). The resin was washed with DMF (5×1 min) and then divided into two portions (2 mmol and 3 mmol divided by volume). The larger portion (3 mmol) was used below (b).

(b) Deprotection and Cyclization Conditions

A portion of the protected resin sample (Method 2a, above) was deprotected using wash cycle B and then successively with $CH_2Cl_2$ (×5), diethylether (×5), and dried under nitrogen. The resin was treated with 5% hydrazinc hydrate in methanol (v/v, 100 ml) for 18 h and the solution removed by filtration. The remaining resin was washed thoroughly with DMF and the combined methanol and DMF washings were evaporated to dryness. The crude hexapeptide hydrazide was desiccated overnight over $H_2SO_4$ and $P_2O_5$ (1.72 g, 2.16 mM) hplc RT=13.4 min.

To the crude hexapeptide hydrazide (1.72 g 2.16 raM) in DMF (50 ml) was added 9.3 M HCl/THF (1.16 ml, 10.8 mmol). The solution was cooled to −25° C. under an atmosphere of nitrogen. Isopentyl nitrite (0.43 ml) was added and after 1 h at −25° C. no trace of starting material was visible by means of hplc. The solution was diluted with pre-cooled (−25° C.) DMF (2.51) and $Et_3N$ added until pH=8.5–9.0 (6 ml) before being left at −20° C. for 2 days. The DMF was removed by evaporation and to the residue was added water. The cream solid which formed was collected by filtration cyclic hexapeptide (1.25 g) hplc $R_t$=17.5 min. and was desiccated over $P_2O_5$ to yield the crude A sample of this material (50 mg) was purified by repeated reverse-phase chromatography on LICHO-PREP C-18 (25–40 μM particle size) eluting the product with a linear gradient of $H_2O$: $CH_3CN$: TFA (from 90:10: 0.1, 500 ml) to 10:09: 0.1, 500 ml) to yield purified cyclic peptide 40 mg.

EXAMPLE 4

Cyclo (Gly-Gln-Trp-Phe-(R)Gly[ANC]Leu-Met)

The preparation of the title compound was similar to that described in Example 1 except that Fmoc was used for the final residue (instead of Boc) and this terminal protecting group was removed prior to removal of the peptide from the solid phase resin. The preparation serves as a general procedure for Examples 4, 7, 8, 9. Thus resin-bound protected peptide Fmoc Trp-Phe-(R)Gly[ANC-2]Leu-Met (0.48 mmol, prepared as in Example 1) was deprotected (wash cycle B) and acylated using Fmoc-L-Gln-ONp in the presence of 1-hydroxybenzo-atriazole in DMF (20 ml) for 60 min. After deprotecting the resin (wash cycle B) it was acylated using the preformed symmetrical arthydride of Fmoc-Gly (2.85 mmol) for 1 h and finally deprotected (wash cycle B). The deprotected peptide was cleaved from the resin with hydrazine hydrate (5% in methanol; 50 ml) for 16 h. The solution was filtered and exhaustively dried to remove the hydrazine and the crude peptide hydrazide was cyclized as described in Example 1b. The peptide was purified chromatographically by gradient elution on silica gel (E. MERCK, LOBAR size "C" 4.4 ml/min from chloroform (500 ml) to chloroform: methanol: acetic acid (85:10:5; 500 ml) which gave the title compound with estimated purity=97% (hplc), amino acid analysis Gly(0.93), Glu(1.01), Phe(1.06) (see footnote).

EXAMPLE 5

Cyclo (Gln-D-Trp-(N-Me)Phe-(R)Gly[ANC-2]Leu-Met) (A) and cyclo (Gln-D-Trp-(N-Me)Phe-(R)Gly[ANC-2]Leu-Met$_2$ (B)

The general procedure as described (Example 1) was used to prepare the title compound. The sequential coupling of Fmoc-Met (1b) and Boc(R)Gly[ANC-2]LeuOH (16h) were as described. Fmoc-(N-Me)Phe (1.5 h) and Fmoc-D-Trp (22.5 h) were both coupled as their symmetrical arthydride and Boc-Gln-ONp (2 h) active ester coupled in the presence of hydroxybenzotriazole. After washing, the protected peptide was removed from the resin by treatment with 5% methanolic hydrazine hydrate. The protected peptide hydrazide obtained after evaporation of the filtrate was deprotected and cyclized as described (Example 1b). Analytical HPLC (U-BONDAPAK) indicated the presence of two major products. These were separated by silica gel chromatography and crystallization.

The later eluting product on analytical HPLC (U-BONDPAK) (A) had the correct molecular weight for the monomeric cyclic peptide by both mass spectrometry (FAB, positive ion m/e=825 (m+Na), negative ion m/e=801 (m−H) and gel filtration (SEPHADEX G-15, in 50% aqueous acetic acid) and was consistent with the structure by ($^1$H) NMR (360 MHz).

The earlier eluting peak (by HPLC on U-BOND-PAK) had the correct molecular weight for the dimeric material (B) by both mass spectrometry (FAB positive ion m/e=1628 (m+Na) and gel filtration (SEPHADEX G-15. in 50% aqueous acetic acid) and was consistent with the structure by ($^1$H) NMR (360 MHz).

EXAMPLE 6

Acetyl-Leu-Met-Gln-Trp-Phe-Gly-NH$_2$

Preparation of the Fmoc-protected hexapeptide resin has been described (Example 3, method 2a). This resin was deprotected by the use of wash cycle B, acetylated with 1% acetic anhydride in DMF (35 min) and then removed from the resin by treatment with methanol saturated with ammonia at 0° C. (16 h). The solution was filtered and the residual resin washed with methanol. The combined filtrates were evaporated to dryness and the residue chromatographed on silica gel (E. MERCK, LOBAR, size C) under isocratic conditions (chloroform: methanol 4:1 at 7 ml/min). The fraction containing product were evaporated to give the title compound (amino-acid analysis Leu (0.97), Met (1.0), Gln (1.01), Phe (1.0), Gly (1.02)).

EXAMPLE 7

Cyclo (Gly-Gln-Phe-Phe-(R)Gly[ANC-2]Leu-Met)

The title compound was prepared in an analogous manner to that described in Example 4. Amino acid analysis gave Glu (1.00), Gly (0.93), Phe (2.07) (see footnote), FAB mass spectroscopy (negative ion) m/e=805 (m−H).

EXAMPLE 8

Cyclo (Gly-Gln-D-Trp-Phe-(R)Gly[ANC-2]Leu-Met)

The title compound was prepared in an analogous manner to that described in Example 4. Amino acid analysis gave Glu(1.01), Gly (1.01), Met (0.95) Phe (1.03).

EXAMPLE 9

Cyclo (Gly-Gln-Tyr-Phe-(R)Gly[ANC-2]Leu-Met)

The title compound was prepared in an analogous manner to that described in Example 4. Amino acid analysis gave Glu (0.99), Gly (1.05) Tyr (0.97) Phe (0.99) and FAB spectroscopy (negative ion) m/e=822 (m−H), positive ion m/e=824 (m+H).

EXAMPLE 10

Cyclo (Gln-Phe-Phe-(R)Gly[ANC-2]Leu-Met)

The title compound was prepared in an analogous manner to that described in Example 1. Amino acid analysis gave Glu (0.98), Phe (2.05), Met (0.97) and FAB mass spectroscopy (negative ion) m/e=748 (m−H), positive ion m/e=750 (m+H).

Footnote

The hydrolysis product from the lactam unit often coeluted with the methionine, and the tryptophan was degraded. Consequently these residues are often not quoted in the amino acid analyses.

EXAMPLE 11

Pharmaceutical Formulation

An injectable suspension was prepared comprising the following ingredients:

| | |
|---|---|
| Cyclo(Gln—Trp—Phe—Gly—Leu—Met) | 1.0 mg |
| Methylcellulose | 5.0 mg |
| TWEEN 80 | 0.5 mg |
| Benzyl alcohol | 9.0 mg |
| Methyl paraben | 1.8 mg |
| Propyl paraben | 0.2 mg |
| Water for injection to a total volume of | 1 ml. |

We claim:

1. A peptide of the formula (I):

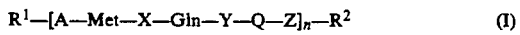

$$R^1-[A-Met-X-Gln-Y-Q-Z]_n-R^2 \qquad (I)$$

in which any of the amide linkages between the amino acids is optionally N-methylated; and wherein A represents Leu;

X represents Gly or a bond;

Y represents an aromatic amino acid residue selected from the group consisting of Trp, D-Trp, Phe, Tyr and Npa;

Q represents a hydrophobic amino acid residue selected from the group consisting of Trp, D-Trp, Phe, Tyr, Npa, Ile and Val;

Z represents Gly;

n is 1 or 2;

$R^1$ represents an amino blocking group; and $R^2$ represents a carboxyl blocking group; or $R^1$ and $R^2$ together represent a bond between the carboxyl group of Z and the amino group of A; or Z and A, optionally together with the bond $R^1$-$R^2$, form a moiety of formula (II):

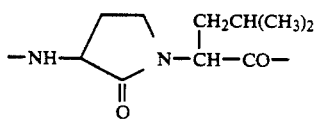  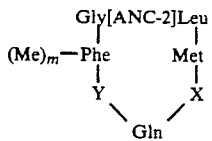

2. The peptide according to claim 1 wherein Y is selected from the group consisting of Trp, D-Trp, Phe and Npa.

3. The peptide according to claim 1 wherein Q represents Phe.

4. The peptide according to claim 1, wherein the amide bond between the groups Y and Q is N-methylated.

5. The peptide according to claim 1, wherein $R^1$ represents acetyl or benzyloxycarbonyl.

6. The peptide according to claim 1, wherein $R^2$ represents amino.

7. The peptide according to claim 1 represented by formula (III):

wherein m is zero or 1; and X and Y are as defined in claim 1.

8. The peptide according to claim 7, wherein Y is selected from the group consisting of Trp, D-Trp, Phe and Npa.

9. A peptide according to claim 1 selected from:
cyclo(Gln-Trp-Phe-(R)Gly[ANC-2]Leu-Met);
cyclo(Gln-Npa-Phe-(R)Gly[ANC-2]Leu-Met);
cyclo(Gln-Trp-Phe-Gly-Leu-Met);
cyclo(Gly-Gln-Trp-Phe-(R)Gly[ANC-2]Leu-Met);
cyclo(Gln-D-Trp-(N-Me)Phe-(R)Gly[ANC-2]Leu-Met);
cyclo(Gln-D-Trp-(N-Me)Phe-(R)Gly[ANC-2]Leu-Met)$_2$;
acetyl-Leu-Met-Gln-Trp-Phe-Gly-NH$_2$;
cyclo(Gly-Gln-Phe-Phe-(R)Gly[ANC-2]Leu-Met);
cyclo(Gly-Gln-D-Trp-Phe-(R)Gly[ANC-2]Leu-Met);
cyclo(Gly-Gln-Tyr-Phe-(R)Gly[ANC-2]Leu-Met); and
cyclo(Gln-Phe-Phe-(R)Gly[ANC-2]Leu-Met).

* * * * *